(12) United States Patent
Vilendrer

(10) Patent No.: US 7,410,792 B2
(45) Date of Patent: Aug. 12, 2008

(54) INSTRUMENTED BIOREACTOR WITH MATERIAL PROPERTY MEASUREMENT CAPABILITY AND PROCESS-BASED ADJUSTMENT FOR CONDITIONING TISSUE ENGINEERED MEDICAL PRODUCTS

(75) Inventor: Kent Vilendrer, Eden Prairie, MN (US)

(73) Assignee: St3 Development Corporation, Eden Prairie, MN (US)

( * ) Notice: Subject to any disclaimer, the term of this patent is extended or adjusted under 35 U.S.C. 154(b) by 710 days.

(21) Appl. No.: 10/944,462

(22) Filed: Sep. 17, 2004

(65) Prior Publication Data
US 2005/0153436 A1 Jul. 14, 2005

Related U.S. Application Data

(60) Provisional application No. 60/504,049, filed on Sep. 19, 2003.

(51) Int. Cl.
C12M 1/36 (2006.01)
C12M 1/00 (2006.01)
C12M 1/12 (2006.01)
C12M 5/02 (2006.01)

(52) U.S. Cl. ............ 435/286.1; 435/284.1; 435/289.1; 435/297.2; 435/394

(58) Field of Classification Search .............. 435/286.1, 435/284.1, 289.1, 297.2, 394
See application file for complete search history.

(56) References Cited

U.S. PATENT DOCUMENTS

| | | | |
|---|---|---|---|
| 5,665,594 A | 9/1997 | Schwarz et al. | |
| 5,670,708 A * | 9/1997 | Vilendrer | 73/37 |
| 5,792,603 A | 8/1998 | Dunkelman et al. | |
| 5,843,766 A | 12/1998 | Applegate et al. | |
| 5,846,828 A | 12/1998 | Peterson et al. | |
| 5,902,937 A | 5/1999 | Amrani et al. | |
| 6,001,643 A * | 12/1999 | Spaulding | 435/298.2 |
| 6,008,049 A | 12/1999 | Naughton et al. | |
| 6,060,306 A | 5/2000 | Flatt et al. | |
| 6,121,042 A | 9/2000 | Peterson et al. | |
| 6,171,812 B1 | 1/2001 | Smith et al. | |
| 6,210,957 B1 | 4/2001 | Carpentier et al. | |

(Continued)

FOREIGN PATENT DOCUMENTS

EP 1186653 3/2002

(Continued)

OTHER PUBLICATIONS

Peng, Xinqi, et al., "In Vitro System to Study Realistic Pulsatile Flow and Stretch Signaling in Cultured Vascular Cells", *Am J Physiol Cell Physiol*, vol. 279,(2000),C797-C805.

(Continued)

*Primary Examiner*—Walter D. Griffin
*Assistant Examiner*—Lydia Edwards
(74) *Attorney, Agent, or Firm*—Nikolai & Mersereau, P.A.; C. G. Mersereau

(57) ABSTRACT

A microprocessor controlled and instrumented bioreactor for conditioning tissue engineered medical products. The microprocessor control providing measurement and control of the tissue displacement and subsequent determination of material and growth properties. The microprocessor control providing adaptive adjustment of the applied conditions to provide optimal tissue growth.

32 Claims, 9 Drawing Sheets

U.S. PATENT DOCUMENTS

| | | | |
|---|---|---|---|
| 6,357,303 | B1 | 3/2002 | Smith et al. |
| 6,416,995 | B1 * | 7/2002 | Wolfinbarger ............ 435/289.1 |
| 6,632,658 | B1 | 10/2003 | Schoeb |
| 6,827,682 | B2 | 12/2004 | Bugge et al. |
| 2002/0037580 | A1 | 3/2002 | Schoeb |
| 2003/0199083 | A1 * | 10/2003 | Vilendrer et al. ......... 435/297.2 |
| 2004/0219659 | A1 | 11/2004 | Altman et al. |
| 2005/0019748 | A1 | 1/2005 | Ochi et al. |

FOREIGN PATENT DOCUMENTS

| | | |
|---|---|---|
| WO | WO-97/39624 | 10/1997 |
| WO | WO-01/68800 | 9/2001 |

OTHER PUBLICATIONS

Wittstein, Ilan S., et al., "Opposite Effect of Pressurized Steady Versus Pulsatile Perfusion on Vascular Endothelial Cell Cytosolic pH", *Circulation Research*, vol. 85,(2000),1230-1236.

Altman, Gregory H., et al., "Advanced Bioreactor with Controlled Application of Multi-Dimensional Strain for Tissue Engineering", *Journal of Biomechanical Engineering*, vol. 124,(Dec. 2002),742-749.

Sodian, R , et al., "New Pulsatile Bioreactor For Fabrication of Tissue-Engineered Patches", *Journal of Biomedical Materials Research*, vol. 58, No. 4, (2001),401-405.

* cited by examiner

Servocontrolled Bioreactor

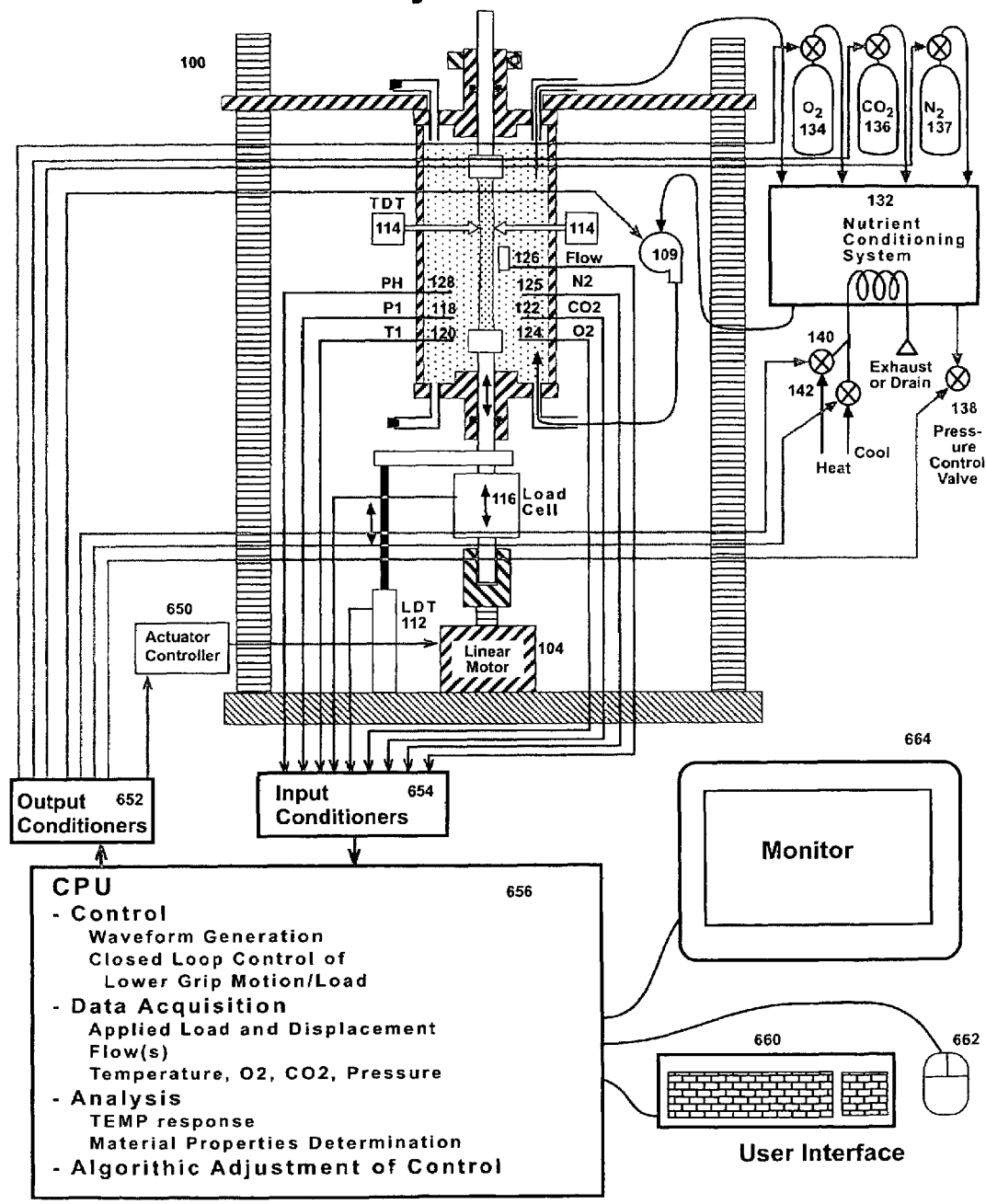
Figure 2- Servocontrolled Bioreactor System Functional

Servocontrolled Bioreactor
with Process-Based Adjustment

Servocontrolled Bioreactor
with Process-Based Adjustment

Figure 4
TEMP Response
Figure 4A - Early in Conditioning Process
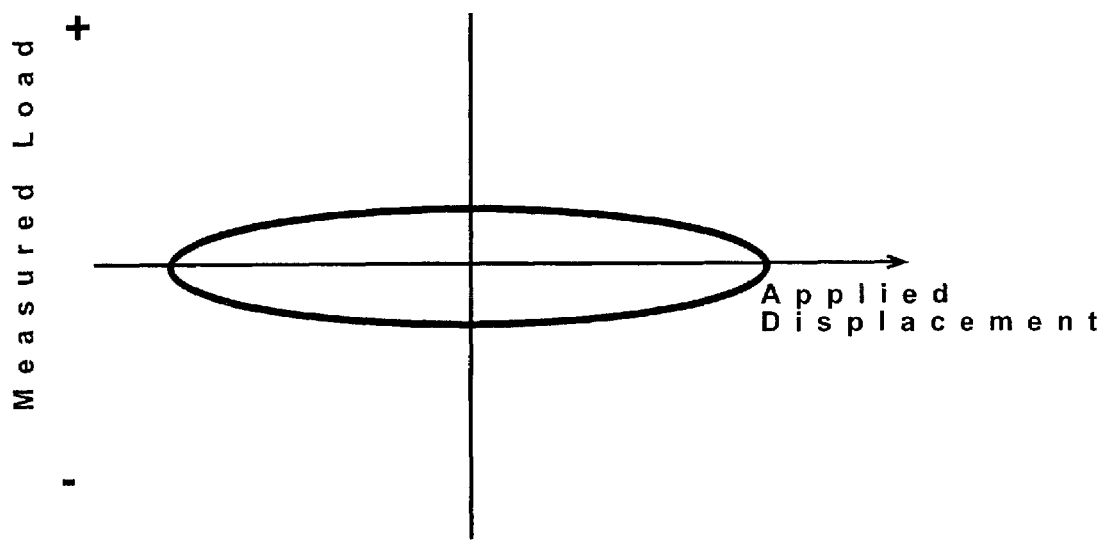
Figure 4B - Late in Conditioning Process
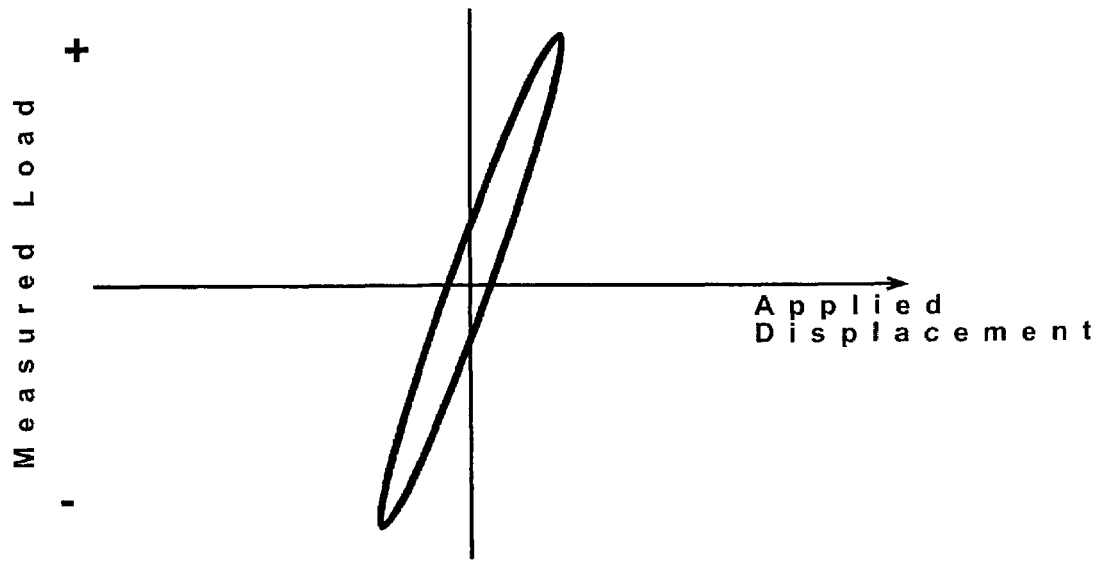

Multi Actuator/ Multi Chamber Servocontrolled Bioreactor

Soft Clamp Detail

Possible Algorithm

INSTRUMENTED BIOREACTOR WITH MATERIAL PROPERTY MEASUREMENT CAPABILITY AND PROCESS-BASED ADJUSTMENT FOR CONDITIONING TISSUE ENGINEERED MEDICAL PRODUCTS

RELATED APPLICATIONS

This application claims the benefit of U.S. Provisional Application Ser. No. 60/504,049, filed Sep. 19, 2003, the entire specification of which is incorporated by reference herein in its entirety.

This application is related to U.S. patent application Ser. No. 10/371,175, filed Feb. 19, 2003, Provisional Patent Application Ser. No. 60/429,583, filed Nov. 27, 2002, Provisional Patent Application Ser. No. 60/364,500, and PCT Application Ser. No. PCT/US03/08197, the entire specifications of which are all incorporated by reference in their entirety.

FIELD OF THE INVENTION

This disclosure relates to method and apparatus for growing and conditioning orthopedic tissue engineered medical products and in particular to method and apparatus for an instrumented and servocontrolled bioreactor with material property measurement capability and process-based adjustment for conditioning tissue engineered medical products (TEMPs).

BACKGROUND

Tissue engineering is a rapidly growing area that seeks to create, repair and/or replace tissues and organs by using combinations of cells, biomaterials, and/or biologically active molecules. It is an interdisciplinary field that integrates aspects of engineering, and other quantitative sciences, with biology and medicine. Research and technology development in tissue engineering promises to revolutionize current methods of health care treatment and significantly improve the quality of life for millions of patients. As one indication of the scope of the problem that tissue engineering addresses, worldwide organ replacement therapies utilizing standard organo-metallic devices consume 8 percent of medical spending, or approximately $350 billion per year. Organ transplantation is another option for replacing damaged or diseased tissue, but one that is severely limited by donor availability. Tissue-engineered products hold the promise for true functional replacement at affordable cost. However, despite early successes, few functional tissue engineered products are currently available for clinical use.

Researchers have sought to develop living alternatives to traditional "man-made" medical devices. These tissue engineered medical products (TEMPs) use the patients own cells to create a replacement device that can be nurtured and grown once they are implanted. Through design, specification, and fabrication of cells, biomaterials, or biomolecules, it is hoped that TEMPs will play a major role in many future surgeries. In the orthopedic area considerable energy is being expended on the development of tissue engineered ligaments, tendons, cartilage or meniscus replacements. Likewise, similar efforts are being made to develop new replacements for heart valves, arteries, heart muscle tissue and venous valves. Tissue engineered replacements for secretory organs such as the liver, kidney and skin also hold great promise for future therapies. Tissue engineered skin replacements are already available and are dramatically improving the outcomes for burn victims and cosmetic therapy.

There is a need in the art for method and apparatus for growing and conditioning tissue engineered orthopedic and medical products.

SUMMARY

The present invention addresses the need in the art for method and apparatus for growing and conditioning tissue and other needs which will be appreciated by those of skill in the art upon reading and understanding the teachings of the present invention.

The present subject matter relates to a bioreactor for conditioning tissue in various embodiments including a bioreactor chamber, the bioreactor chamber including at least one clamp for holding the tissue, at least one means of linear, rotary, shear, pressure, flow, or thermal actuation to the tissue or tissue environment; and microprocessor real-time control means for measuring and controlling the applied actuation condition and for measuring the response of the TEMP, wherein the microprocessor control means provides analysis of the tissue material properties and other cell growth rate and subsequent process-based adjustment of the actuation conditions based upon the tissue material properties and growth properties, as described in the detailed description and recited in the claims.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIG. 2 is a functional diagram of the microprocessor servocontrolled bioreactor system shown in FIG. 1 according to one embodiment of the present subject matter.

FIG. 4A shows a plot demonstrating one example of axial load versus applied strain for an orthopedic TEMP early in a mechanical conditioning process according to one embodiment of the present subject matter.

FIG. 4B shows a plot demonstrating one example of axial load versus applied strain for an orthopedic TEMP late in a mechanical conditioning process according to one embodiment of the present subject matter.

DETAILED DESCRIPTION

Figure 1:
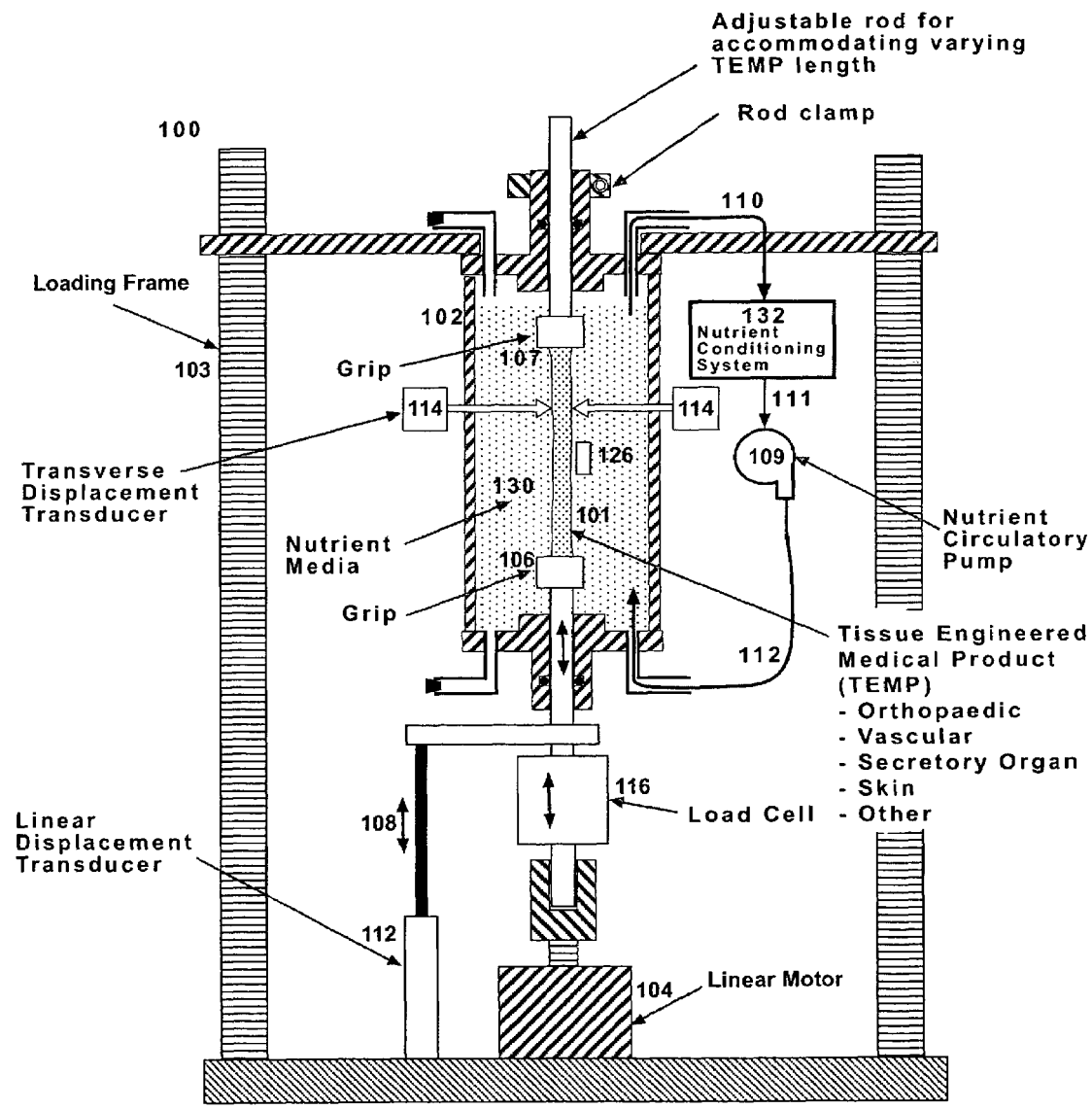
FIG. 1 is one embodiment of a microprocessor servocontrolled bioreactor according to one embodiment of the present subject matter. In one application of this embodiment, which is not exclusive or limiting, it conditions orthopedic TEMPs.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

The present disclosure relates to method and apparatus for an instrumented bioreactor with material property measurement capability and process-based adjustment for conditioning tissue engineered medical products (TEMPS).

This detailed description incorporates by reference in its entirety U.S. patent application Ser. No. 10/371,175 by Vilendrer et al., filed Feb. 19, 2003, entitled "Bioreactor with Plurality of Chambers for Conditioning Intravascular Tissue Engineered Medical Products." This detailed description also incorporates by reference in its entirety U.S. Provisional Patent Application Ser. No. 60/364,500, by Vilendrer et al., filed Mar. 15, 2002, entitled "Instrumented/Servocontrolled Bioreactor for Conditioning Intravascular Tissue Engineered Medical Products (TEMPS)."

This disclosure relates to method and apparatus for growing and conditioning orthopedic tissue engineered medical products and in particular to method and apparatus for an instrumented and servocontrolled bioreactor with material property measurement capability and process-based adjustment for conditioning tissue engineered medical products (TEMPs). TEMPS can be in the areas including, but not limited to, the orthopedic, vascular and secretory organ areas. TEMPs within the orthopedic area could include ligaments, tendons, cartilage, meniscus and other muscleo-skeletal devices. Within the vascular area TEMPs could include arterial conduits, shunts, venous valves, heart valves, heart muscle and other devices. Within the secretory organ area TEMPs could include liver, kidney, skin and other organs.

TEMPs are typically comprised of a collagen matrix that is populated with multiple layers of cells. Depending upon the TEMP type, these cells could include muscle, fibroblasts, endotheal or other types of cells. The matrix provides a structure that the cells can grow on. In order for the cells to grow, they must be exposed to a nutrient environment. An environment where the cells could grow and multiply rapidly is desirable. Furthermore, properly imparting mechanical stresses and strains or changing conditions into the cells stimulates faster growth, orientation and enhanced material properties. For example, mechanical strain applied to fibroblasts seeded on collagen cells, induces fibroblast elongation and alignment of the cells. Mechanical strain also promotes smooth muscle cell proliferation.

FIG. 1 provides one embodiment of a servocontrolled bioreactor configuration 100 for growing and conditioning orthopedic tissue engineered medical products (TEMPs), including, but not limited to, ligaments, tendons, cartilage, meniscus and other muscleo-skeletal devices. In the example of FIG. 1 it is noted that the TEMP (or bioprosthesis) 101 is elongated. In other embodiments the bioprosthesis 101 is irregularly shaped (ie: cartilage or meniscus), since the bioprosthesis 101 does not have to be elongated to operate in accordance with the system.

The system 100 shown in FIG. 1 and FIG. 2 includes a bioreactor chamber assembly 102 and a computer controlled motorized frame 103 driven by a linear motor 104. The linear motor 104 drives a lower grip assembly 106 to produce a mechanical strain as demonstrated by arrow 108. This embodiment also includes a circulatory pump 109, which provides a continuous flow of nutrient 130, as shown by the arrows 110, 111 and 112. The nutrient flow is refreshed via nutrient conditioning system 132. This embodiment includes, but is not limited to, nine transducers 112, 114, 116, 118, 120, 122, 124, 126 and 128. The transducers provide measurements including, but not limited to, linear displacement 112 (axial strain), and load 116 (axial stress) along the longitudinal axis of the bioprosthesis 101. Other mechanical transducers include transverse displacement 114 (for measuring transverse strain) and axial flow velocity 126 (for determining surface shear stress) on the bioprosthesis. Other measurements and sensors (not shown) include but are not limited to pressure 118, temperature 120, $CO_2$ 122, $O_2$ 124, pH 128 of the surrounding media and $N_2$ 125. In one embodiment, an adjustable rod is connected to an upper grip 107. The adjustable rod can accommodate various TEMP lengths. A rod clamp is set to place the rod in an adjustable position. The TEMPS measured can include orthopedic, vascular, secretory organs, skin, and other TEMPS.

FIG. 2 is a functional diagram showing signals between exemplary bioreactor 100 of FIG. 1, motor amplifier 650, output conditioner 652 and input conditioners 654, and the central processing unit (CPU) 656. Signals from various transducers including 112, 114, 116, 118, 120, 122, 124, 126, 128 are processed and provided to the CPU 656 via input conditioners 654. Signals from linear displacement transducer 112 designated as LDT and representing the linear motor displacement (applied axial strain), a signal from a transverse displacement transducer 114 designated TDT (resulting poisson strain), a signal from load cell 116 representing the resulting bioprosthesis load (resulting mechanical stress), a signal from pressure sensor 118 denoted as P1, a signal denoted as T1 from temperature sensor 120, a signal denoted CO2 from CO2 sensor 122 representing carbon dioxide level, a signal denoted O2 from O2 sensor 124 representing oxygen level, a signal denoted as flow from flow sensor 126 representing the nutrient flow rate along the surface of the bioprosthesis, a signal denoted pH from pH sensor 128 representing the pH level of the nutrient are sent to the CPU 656 via input conditioners 654, a signal denoted N2 from N2 sensor 125 representing nitrogen level. Other sensors and measurements may be made without departing from the teachings of the present application.

Output signals from output conditioners 652 are provided to the nutrient conditioning system 132, nutrient circulatory pump 109, and motor amplifier 650. For the nutrient conditioning system 132, separate outputs are provided for controlling the $O_2$, $CO_2$ and $N_2$ levels, Pressure, and Heating and Cooling inputs. It is understood that signals may be transmitted to the transducers 112, 114, 116, 118, 120, 122, 124, 125, 126 and 128 as needed to implement the desired signal sensing. It is also understood that in varying embodiments, conditioning means may be used for each transducer for proper signal generation.

The CPU 656 couples to a user environment via a user interface. The user interface may include a keyboard 660, a mouse 662 or other select device, and a monitor 664.

In varying embodiments the CPU 656 is capable of controlling several operations, including, but not limited to:

Linear Motor Control: The CPU 656 monitors the linear motor displacement using LDT 112 that is connected to the motor output shaft. It uses this signal as the feedback in a digital PID loop. The output signal from the PID loop drives the motor amplifier 650, which in term drives the linear motor 104. The CPU 656 also creates an input waveform for the PID loop. This waveform can be any shape and it is created by the user using simple segments (sines, ramps, square or other waveform) or discrete points.

Nutrient Circulatory Pump Control: In another control loop, the CPU 656 monitors the flow conditions and adjusts the flow rate produced by the nutrient flow pump. The flow rate includes, but is not limited to, a signal from flow transducer 126 or the pump volumetric output (assumes calibrated pump with speed output).

Nutrient Conditioning Subsystem Control: The CPU 656 monitors the $CO_2$, $O_2$, $N_2$, pH, temperature and pressure levels. These parameters can be controlled by the Nutrient Conditioning System 132. The CPU 656 can alter the levels of the $O_2$, $CO_2$ and $N_2$ that are injected into the nutrient system 132 via the $O_2$ 134 and $CO_2$ 136 and $N_2$ 137 Injection Systems. In addition, the CPU 656 can alter the nutrient pressure via the Pressure Control Valve 138. Likewise the CPU 656 can alter the temperature by introducing heating and cooling media into the system via heating 140 and cooling 142 subsystems. Alternatively, the nutrient control parameters can be controlled by either placing the entire bioreactor 100 into an incubator, by routing preconditioned nutrient media from an incubator into the bioreactor 100, or by refreshing the current nutrients in the loop with new preconditioned nutrients. Note that FIG. 2 shows the pressure, temperature, $CO_2$, $O_2$, $N_2$, and pH sensors located within bioreactor chamber 102. These could also be located in the nutrient 30 conditioning subsystem 132.

Data Acquisition of all Transducers: The CPU 656 provides data acquisition for all sensors. To avoid any acquisition aliasing the acquisition rate is generally in the 2 to 8 kHz range. Other acquisition ranges are possible without departing from the scope of the present system.

Checking for Out of Tolerance Conditions: The CPU 656 checks all of the transducer readings to ensure that they are within certain desired conditions. For example, if the applied load drops dramatically, this might indicate that there is a tear in the bioprosthesis 101. Alternatively, if the pressure increases substantially, this might indicate that the nutrient flow loop is plugged.

Graphical Interface and User Input: The CPU 656 provides all of the transducer information in a graphical format making it easy for an operator to see what is happening with the process. The transducer waveforms and control signals can all be plotted with respect to time or one another. The instantaneous transducer readings also can be viewed. The interface also enables the user to set up the conditioning waveform and other parameters. These settings can be used for conditioning subsequent bioprostheses.

Figure 3A:
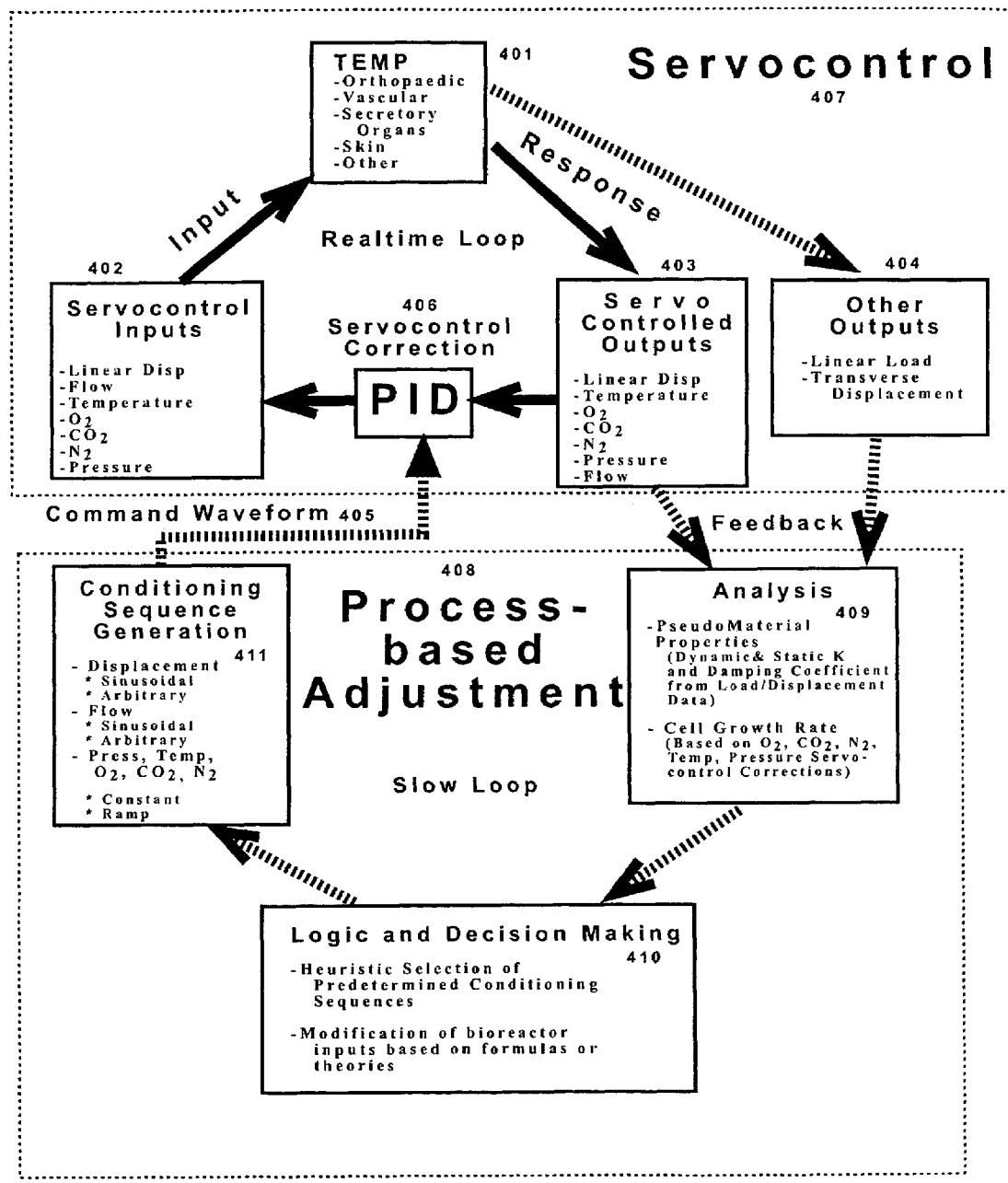
FIGS. 3A and 3B show a functional diagram showing the control, measurement, analysis and process-based correction according to one embodiment of the present subject matter.

Servocontrol and Process-Based Adjustment: FIG. 3A shows a flow diagram of the servocontrol 407 and process-based adjustment 408 that take place in this embodiment of the bioreactor system. The following is an explanation of the Servocontrol 407 portion of this diagram. The TEMP (bioprosthesis) 401 may be an orthopaedic, vascular, secretory organ, skin or other bioprosthesis that has been placed within the bioreactor chamber. In this embodiment, the Servocontrol Inputs 402 are Linear Displacement, Flow, Temperature, $O_2$, $CO_2$, and $N_2$ and Pressure. These inputs can be altered by signals sent from the Output Conditioners 652 to the Linear Motor 104, Nutrient Flow Pump 109, Heat 140, Cool 142, $O_2$ Injection 134, $CO_2$ Injection 136, $N_2$ Injection 137, and Pressure Control Valve 138 shown in FIG. 2. Measurements of the Servocontrolled Outputs 403 are taken by the LDT 112, Flow Sensor 126, Temperature Sensor 120, $O_2$ Sensor 124, $CO_2$ Sensor 122, $N_2$ sensor 125 and Pressure Sensor 118 shown in FIG. 2. Likewise, the Bioprosthesis 401 will also exhibit Other Outputs 404 in response to the servocontrolled inputs. For example, as the bioprosthesis 401 becomes stronger, the load measured by Load Cell 116 (FIG. 2) will increase. Likewise, as certain cell groups (ie: fibroblasts) orient along the axis of the bioprosthesis, the transverse displacement of the bioprosthesis outer wall will change with respect to the linear displacement. The CPU 656 (FIG. 2) monitors the Servocontrolled Outputs and compares them to the Command Waveform 405 and makes Servocorrections 406 to Servocontrol Inputs 402 SO that the desired Servocontrolled Outputs 403 are maintained. This can be accomplished using a traditional Proportional, Integral, Derivative (PID) approach. It can also be done using other types of control schemes (ie: fuzzy logic). This scheme represents the servocontrol nature of the bioreactor. It should be noted that the Servocontrol 407 is done on a real-time basis. For example, real-time could be construed as 2,000 to 10,000 updates per second.

The following is a description of the Process-based Adjustment 408. The user is able to program the CPU 656 with a process. The process is composed of Analysis Capability 409, Logic and Decision Making Capability 410, and Conditioning Sequence Generation 411. The Analysis Capability 409 takes the sensor outputs from both the Servocontrolled 403 and Other 404 Outputs and determines the bioprosthesis pseudomaterial properties. The term pseudo is used because of the difficulty associated with measuring the bioprosthesis cross-sectional area and length. Rather than using stress and strain, the terms normally associated with materials properties measurement, the analysis would use terms like stiffness (force/displacement) or relative stiffness (current stiffness with respect to starting stiffness). It should also be noted that the dynamic material properties are important in predicting the in-vivo performance of the bioprosthesis. The dynamic properties are the various stiffness and damping the bioprosthesis will exhibit at various rates or frequencies. For example, the load cycle imparted by a normal footstep to a knee joint or spinal joint is a complex waveform. This waveform can be made up of loading components that range from DC to 20 Hz. It is important in biomaterials and prosthesis design to ensure the material response of the bioprosthesis is closely matched to the native biomaterial. For example, a spinal disk bioprosthesis that is too stiff will place undue loading on the surrounding vertebrae. Likewise, a spinal disk bioprosthesis that is too soft will end up taking too much motion which will lead to early failure. It should also be noted that it is advantageous that the bioprosthesis stiffness match the native tissue across all operating rates or frequencies. For example, the bioprosthesis needs to work just as well during jogging (more high frequency load components) as it does when the patient is sitting behind the wheel (mostly static loading). FIGS. 4A and 4B and the description that follows describe how the bioprosthesis might respond at various stages in the mechanical conditioning process.

The other sensor readings are used to analyze the response of the bioprosthesis to other factors. For example an increase in $O_2$ input required to maintain the $O_2$ level may indicate accelerating cell proliferation. Likewise $CO_2$ is often used to maintain the pH of the nutrient media. A change in the $CO_2$ required to maintain the desired pH may indicate some other growth phenomenon.

Once the the pseudo-material properties of the bioprosthesis are determined, the Logic and Decision 410 occurs. This part of the process uses the material properties to make decisions about what should be done next to the bioprosthesis to optimize it's various attributes. For example, in the first few days of the conditioning process, cells are introduced into the nutrient and circulated throughout the bioreactor chamber. These cells adhere to the bioprosthesis construct and begin growing. As the cells grow they begin using more oxygen. By monitoring the oxygen usage, one could analyze the status of the seeding process. Once the ceeding process has been deemed completed (by means of meeting certain oxygen usage criteria), the first mechanical stimulation stage could be started. The first mechanical stimulation stage could be performed until certain material properties (i.e.,: certain static stiffness) were achieved. Once those conditions were met, the next stage could be started, etc. Alternatively, the process could be of a more continuous nature and by monitoring all the bioprosthesis attributes simultaneously, a formula or theory could be developed that would make continual adjustments to the conditioning process.

Figure 8:
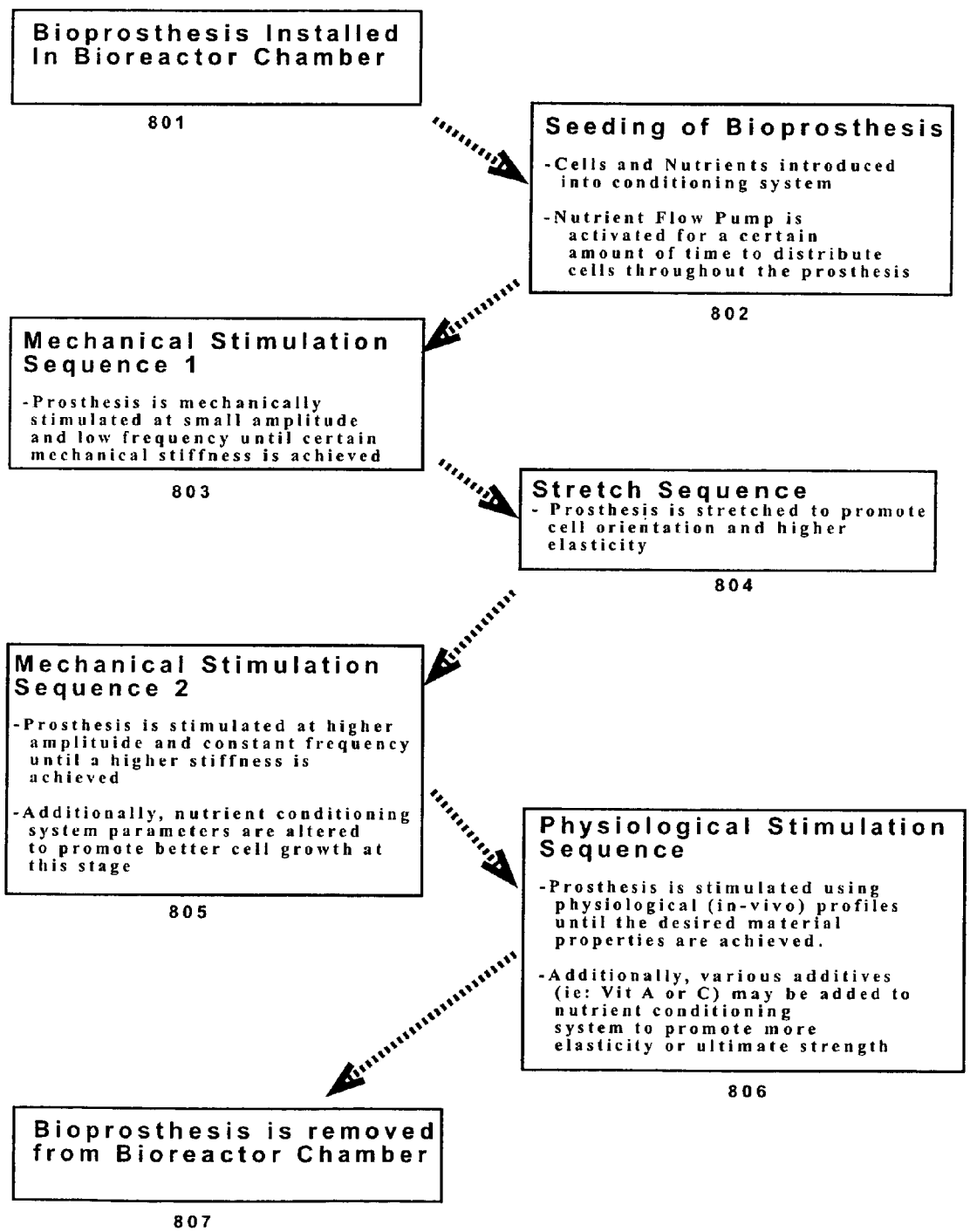
FIG. 8 shows an example process for the bioreactor according to one embodiment of the present subject matter.

The Process-based Adjustment 408 then invokes the Conditioning Sequence Generation 411 to create the Command Waveform 405 for the Servocontrol 407. The Conditioning Sequence Generation may invoke a series of waveforms sequences that have been previously created through experimentation. The waveforms may also have been created "on the fly" by formulas in the Logic and Decision Making 410 portion. The formulas might be used to alter the wave shape (ie: sinusoid, physiological, arbitrary), amplitude or frequency (applies to repeating waveforms). It is expected that the Conditioning Sequence Generation 411 used in the Process can be developed to adapt the conditioning conditions to provide the optimum cell growth rate or strength. This enables the bioreactor 100 (FIG. 2) to grow the bioprosthesis 401 from start to finish with little or no operator supervision. FIG. 8 provides a more detailed description of this.

It should be noted that the Process-based Adjustment 408 does not need to be done on a real time basis since the bioprosthesis grows relatively slowly and it's material properties do not change quickly. For example, this process could be performed hourly.

Figure 3B:
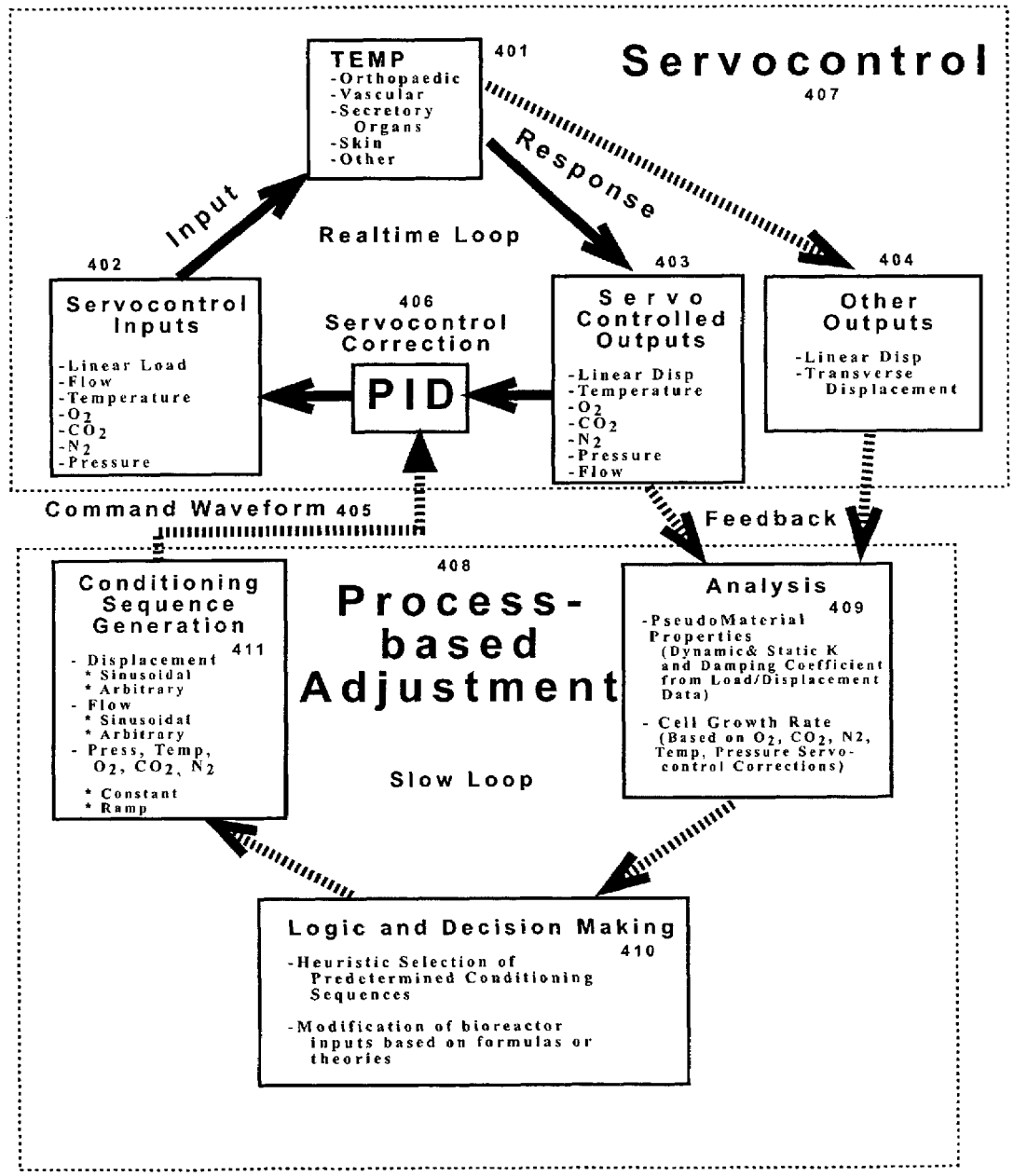

FIG. 3B shows an alternate embodiment of the Servocontrolled Bioreactor with Process Adjustment wherein the Servocontrol Inputs 402 include Linear Load Displacement, Flow, Temperature, $O_2$, $CO_2$, $N_2$ and Pressure. In this case the Linear Displacement that results from the applied load is considered an Other Output. The point of this Figure is to show that any combination of ServoControl Inputs can be used.

Analysis of Bioprosthesis Response and Material Properties: FIGS. 4A and 4B show what the mechanical response of the bioprosthesis 101 might look like in the early and later stages of conditioning.

In the early stages as shown in FIG. 4A, the bioprosthesis is very compliant and the applied displacement (mechanical strain) causes little measured axial load (mechanical stress) response from the bioprosthesis. The biomaterial also behaves very viscous and shows much damping.

In the later stages as shown in FIG. 4B, the bioprosthesis 101 exhibits a "tighter" response. The applied displacement (mechanical strain) creates a higher measured load (mechanical stress) response from the bioprosthesis. The loop is also more closed indicating that the biomaterial is behaving more elastically.

Figure 5:
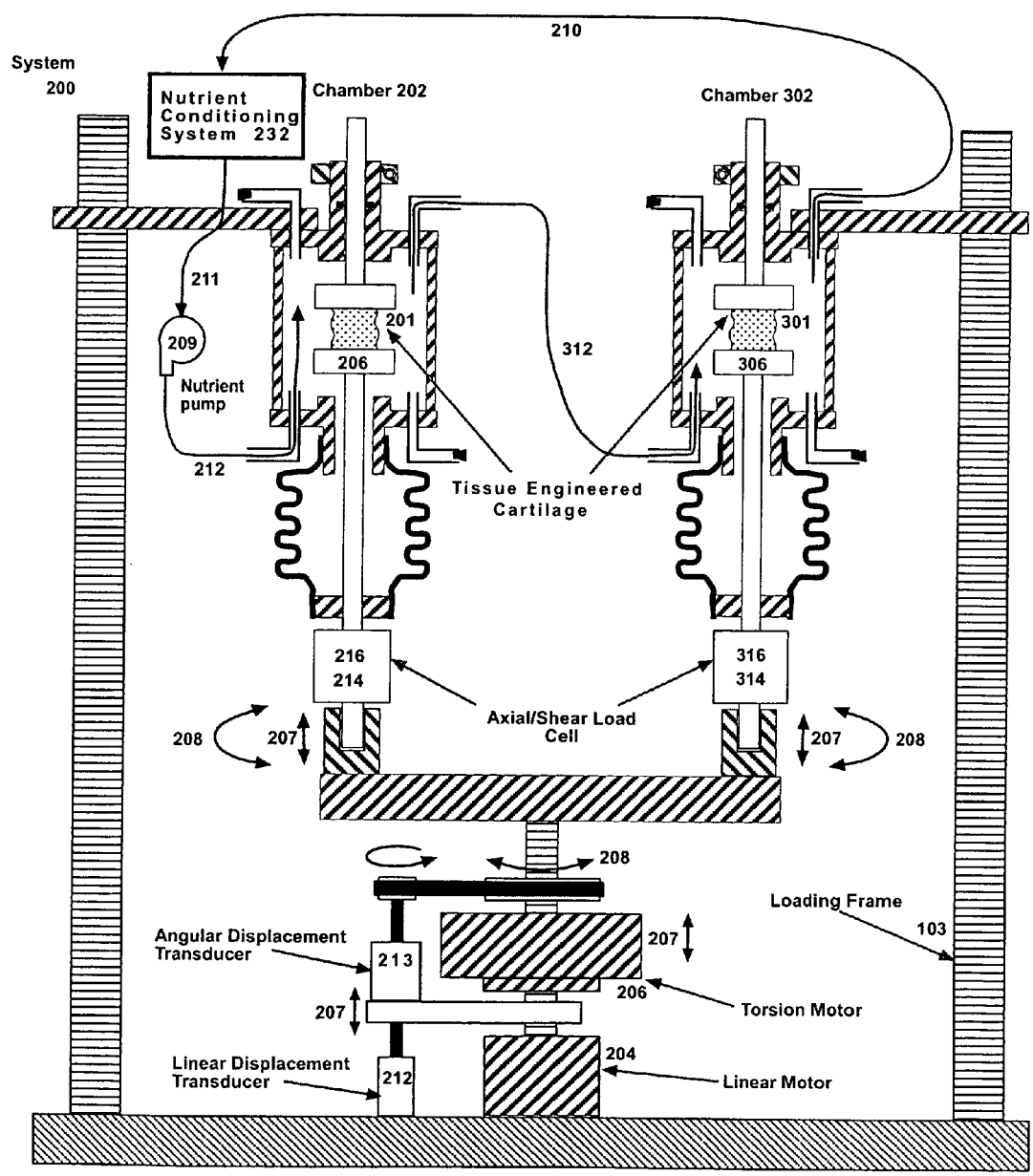
FIG. 5 is a functional diagram of a bioreactor system with multiple means of actuation and multiple bioreactor chambers according to one embodiment of the present subject matter.

The same kind of response may also be measured using the axial or shear displacement and load displacement transducer measurements shown in FIG. 5. Using a Fast Fourier Transform (FFT), the load/displacement response can be separated into the real (elastic) and imaginary (viscous) response components. Other analysis techniques may include, but are not limited to, Neural Networks and systems involving timed domain measurements.

These key components can be used to determine the bioprosthesis 101 (FIG. 2) material properties. This provides an indication of how well the bioprosthesis is responding to the mechanical conditioning process. Measurement of the material properties of the bioprosthesis 101 while within the bioreactor 100 provides numerous advantages. The presented duplicates conditions found in vivo and creates enhanced pseudo-material properties within the bioprosthesis 101. The desired material properties include, but are not limited to, the storage and loss stiffness (modulus of elasticity) as a function of applied strain rate or frequency. These are also referred to as the elastic and viscous components of elasticity and are determined from the force/displacement (stress/strain) measurements. Other material properties include strength, density, chemistry, temperature and more.

FIG. 5 provides another embodiment of a servocontrolled bioreactor configuration 200 for growing and conditioning tissue engineered medical products (TEMPs). In the example of FIG. 5 it is noted that the TEMP (bioprostheses) 201 and 301 are shortened and shown as tissue engineered cartilage. The system 200 shown in FIG. 5 includes multiple bioreactor chamber assemblies 202, 302 and a computer controlled motorized frame driven by linear and torsional motors 204 and 206. One purpose of this Figure is to show that the instrumentation, control and process-based adaptation can be applied to more than one control axis and more than one bioreactor chamber. In this embodiment a single linear motor 204 drives the lower grip assemblies 206, 306 to produce mechanical strain in more than one TEMP as demonstrated by arrow 207. This embodiment also includes a torsion motor to create shear strain in more than one TEMP as demonstrated by arrow 208. This embodiment also includes a nutrient circulatory pump 209, which provides a continuous flow of nutrient as shown by the arrows 210, 211, 212 and 312. This embodiment includes, but is not limited to, twelve transducers 214, 216, 218, 220, 222, 224, 225, 226, 228, 230, 232, 234, 236. The transducers provide measurements including, but not limited to, linear displacement 212 (axial strain), and load 216, 316 (axial stress) along the longitudinal axis of the bioprostheses 201, 301. Other mechanical transducers include angular displacement 213 (for measuring shear displacement normal to bioprosthesis axial axis) and the shear load 214, 314 (for measuring shear stress normal to bioprosthesis axial axis). Other measurements (not shown) include but are not limited to pressure 218, temperature 220, $CO_2$ 222, $O_2$ 224, $N_2$ 225, and pH 228 of the surrounding media and axial flow velocity 226, 326 (for determining surface shear stress) on the bioprostheses 201, 301.

Figure 6:
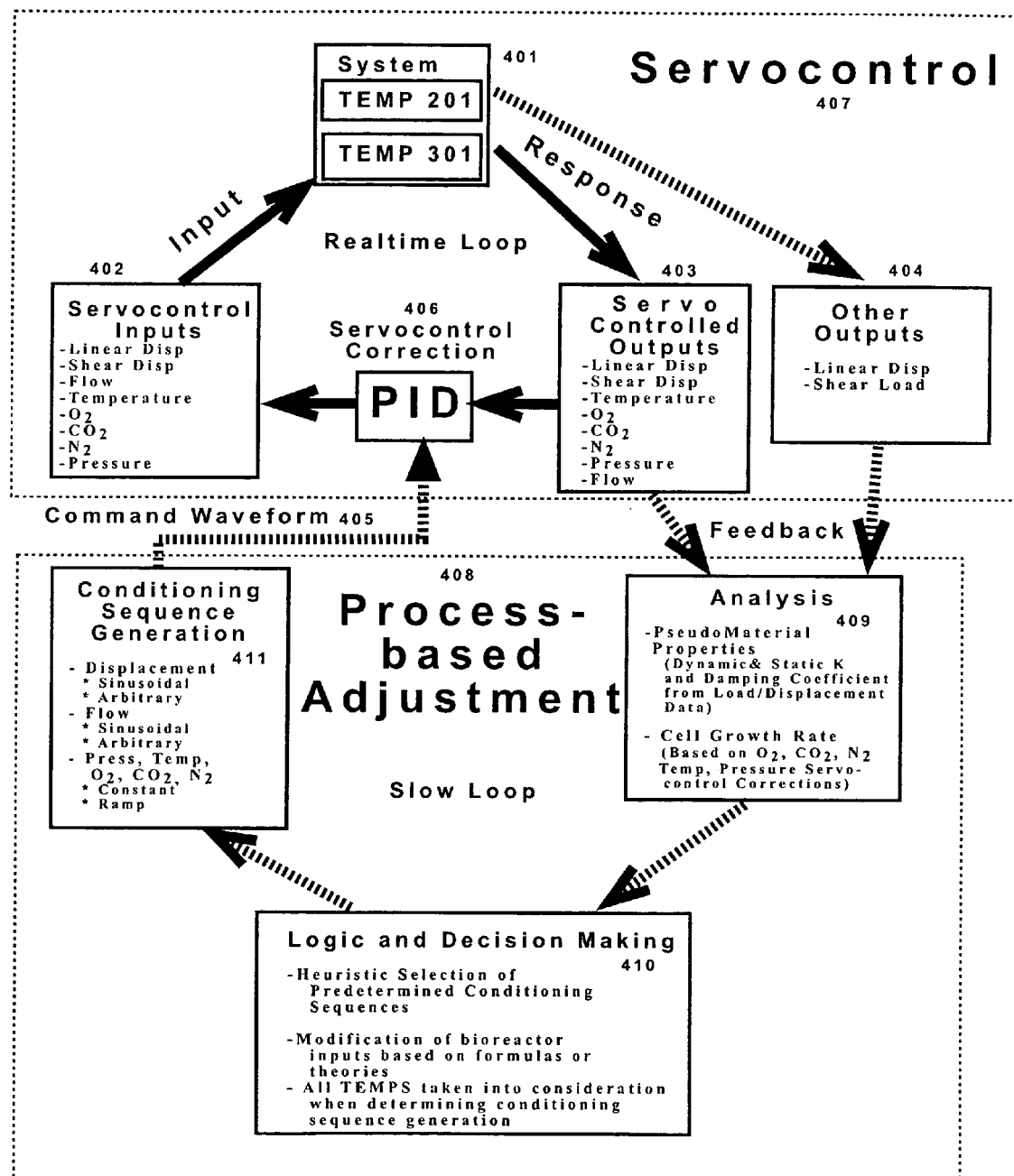
FIG. 6 shows a functional diagram showing the control, measurement, analysis and process-based correction for the embodiment of the bioreactor shown in FIG. 5, according to one embodiment of the present subject matter.

FIG. 6 shows how the Process-Based Adaptation can be applied to more than one axis of motion. In this example, axial and shear displacement are shown.

Figure 7:
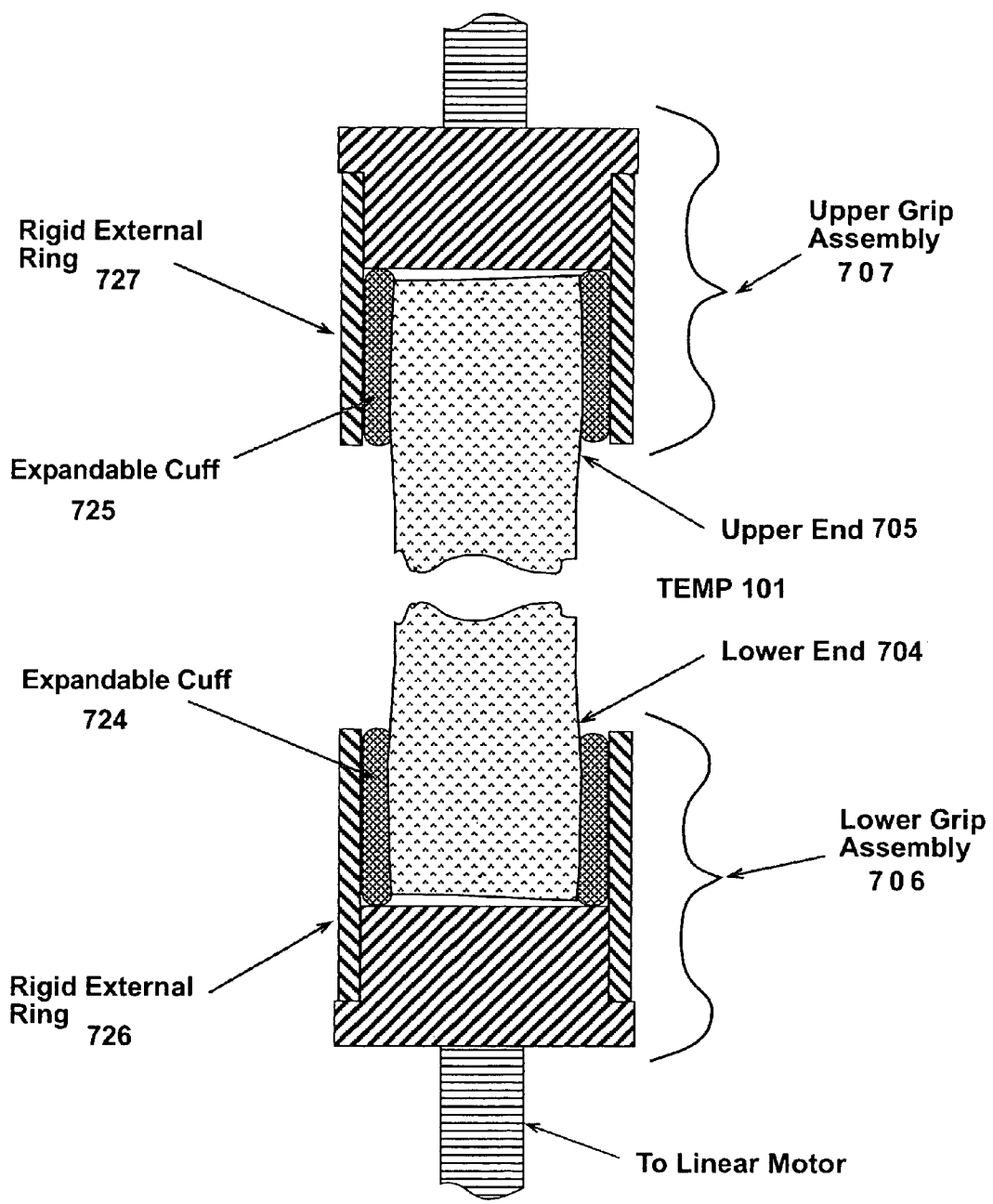
FIG. 7 shows one embodiment of a soft clamp mechanism that may be used to clamp the end of an orthopedic TEMP, according to one embodiment of the present subject matter.

FIG. 7 shows an embodiment where the lower 706 and upper 707 grips use a soft clamp means to hold the bioprosthesis 101 in position. The soft clamps 706, 707 are intended to provide secure attachment of the bioprosthesis 101 without damaging it. In one embodiment, soft clamps 706 and 707 are rubber clamps. In one embodiment, as provided by FIG. 7, the soft clamp 706, 707 includes expandable cuffs 724, 725. In one embodiment the expandable cuffs 724, 725 are inflatable cuffs that mechanically biases the bioprosthesis lower 704 and upper 705 end portions against rigid external rings 726, 727. The inflatable cuffs 724, 725 can exert force, since they are constrained by rigid external rings 726, 727. In one embodiment, the inflatable cuffs 724, 725 are doughnut shaped. In one embodiment, inflatable cuffs 724, 725 are inflated with air. In one embodiment, the inflatable cuffs 724, 725 are inflated with fluid. In varying embodiments, the cuff inflation pressure is controllable. One embodiment incorporates fixed volumetric displacement to create and control inflation pressure. Other expandable cuffs are possible without departing from the scope of the present system. In one embodiment, the rigid external rings 726, 727 have a smooth internal surface. In one embodiment, the rigid external rings 726, 727 have a textured or ridged internal surface to provide better grip on the bioprosthesis end portions 704 and 705. In another embodiment, the rigid external rings 726, 727 are metals. In another embodiment, the rigid external rings 726, 727 are plastic. Other embodiments and biasing systems are possible without departing from the scope of the present soft clamp approach.

FIG. 8 shows an example process for the bioreactor. The following is an explanation of the example process. Other processes are possible without departing from the scope of the present subject matter:

The Bioprosthesis is installed in Bioreactor Chamber 801. A bioprosthesis construct is installed in the chamber and clamped in place using the Soft Clamp demonstrated in FIG. 7 or some other means.

The Seeding of the Bioprosthesis 802 is performed. Living cells are introduced into the Nutrient Conditioning System 132 (as demonstrated by FIG. 2, for one example) and circulated throughout the system via the Nutrient Flow Pump 109 (as demonstrated by FIG. 2, for one example). After some period of time a number of cells adhere to the construct and begin growing. The growth can rates can be determined empirically or possibly by measurement of the oxygenation rates required to maintain the desired oxygen level.

Once the bioprosthesis has been seeded, the Mechanical Stimulation Sequence 1 803 begins. This sequence applies a low amplitude and frequency sinusoidal displacement profile into the prosthesis to promote cell growth and orientation. As the cells grow the construct begins to exhibit increased material properties. Once the desired material properties are achieved, the next sequence begins.

The Stretch Sequence 804 stretches the bioprosthesis for short intervals to promote additional alignment of the fibroblast cells. Once this has been completed and the desired material properties have been achieved, additional cyclic conditioning is required.

The Mechanical Stimulation Sequence 2 805 utilizes a higher amplitude and frequency sinusoidal displacement profile to promote additional cell growth and orientation. As the cells continue to grow they exhibit further increased material properties. Once new desired material properties are achieved, the next sequence begins.

The Physiological Stimulation Sequence 806 uses a physiologic waveshape and levels (what would be found in-vivo) to provide additional conditioning to the bioprosthesis. At this point the operator could monitor the bioprosthesis material properties and add additional nutrients into the system to alter the material properties. For example it has been shown that Vitamin A promotes increased elasticity in tissues while Vitamin C promotes increased stiffness. This sequence is continued until certain new material properties are achieved.

The Bioprosthesis is removed from the Bioreactor Chamber 807. The system is stopped, the chamber removed and the bioprosthesis is removed from the chamber.

The sequences and procedures in this process may vary without departing from the scope of the present subject matter. This description is intended to demonstrate the present subject matter and is not intended an exclusive or limiting sense.

Although specific embodiments have been illustrated and described herein, it will be appreciated by those of ordinary skill in the art that other arrangements can be substituted for the specific embodiment shown. This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A bioreactor for conditioning tissue, comprising:
   (a) a bioreactor chamber, the bioreactor chamber including at least one device for holding tissue;
   (b) actuation system including at least one primary mover for applying a mechanical conditioning to the tissue;
   (c) a plurality of sensors including at least one sensor for measuring the applied mechanical conditioning and at least one sensor for measuring a tissue response to the applied mechanical conditioning and at least one sensor for measuring environmental conditions in said bioreactor chamber;
   (d) a microprocessor control system in communication with the actuation system and plurality of sensors for controlling the applied mechanical conditioning and for monitoring response of the tissue;
   (e) wherein the microprocessor control system provides real time monitoring and control of conditioning for the tissue within the bioreactor chamber; and
   (f) wherein the microprocessor control system is able to programmably adjust or alter conditioning parameters for the tissue within the bioreactor chamber including mechanical and environmental conditioning parameters based on variations of the mechanical response and sensed conditions of the tissue and bioreactor conditions as measured by the plurality of sensors using a programmed process, the programmed process incorporating data concerning the tissue within the bioreactor chamber.

2. A bioreactor as in claim 1, wherein the microprocessor control system controls at least partially based on inputs from a control software.

3. A bioreactor as in claim 1, wherein at the least one means for holding tissue includes a soft clamp.

4. A bioreactor as in claim 1, wherein the microprocessor control system includes a device selected from the group consisting of load monitors and a load monitor and control.

5. A bioreactor as in claim 1, wherein the microprocessor control system includes a device selected from the group consisting of a tissue displacement monitors and a tissue displacement monitor and control.

6. A bioreactor of as in claim 1, wherein the microprocessor control system includes a device selected from the group consisting of tissue stress and strain monitors and a tissue stress and strain monitor and control.

7. A bioreactor as in claim 1, wherein the microprocessor control system includes a device selected from the group consisting of pressure monitors and a pressure monitor and control.

8. A bioreactor as in claim 1, wherein the microprocessor control system includes a device selected from the group consisting of fluid flow monitors and a fluid flow monitor and control.

9. A bioreactor as in claim 1, wherein the microprocessor control system includes a device selected from the group consisting of temperature monitors and a temperature monitor and control.

10. A bioreactor as in claim 1, wherein the microprocessor control system includes a device selected from the group consisting of $O_2$ (Oxygen) monitors and an $O_2$ (Oxygen) monitor and control.

11. A bioreactor as in claim 1, wherein the microprocessor control system includes a device selected from the group consisting of $CO_2$ (Carbon Dioxide) monitor and a $CO_2$ monitor and control.

12. A bioreactor as in claim 1, wherein the microprocessor control system includes a device selected from the group consisting of $N_2$ (Nitrogen) monitor and an $N_2$ (Nitrogen) monitor and control.

13. A bioreactor as in claim 1, wherein the microprocessor control system includes a device selected from the group consisting of pH monitors and a pH monitor and control.

14. A bioreactor as in claim 1, wherein the actuation system includes a linear motor.

15. A bioreactor as in claim 1, wherein the actuation system includes a rotary motor.

16. A bioreactor as in claim 1, wherein the actuation system includes a voice coil motor.

17. A bioreactor as in claim 1, wherein the actuation system includes a servomotor.

18. A bioreactor as in claim 1, wherein the actuation system includes a piezo-motor.

19. A bioreactor as in claim 1, wherein the actuation system includes a solenoid.

20. A bioreactor as in claim 1, wherein the actuation system includes a pneumatic actuator.

21. A bioreactor as in claim 1, wherein the actuation system includes a hydraulic actuator.

22. A bioreactor as in claim 1, wherein the actuation system includes a thermo-mechanical drive.

23. A bioreactor as in claim 1, wherein the actuation system includes a stepper motor-drive.

24. A bioreactor as in claim 1, wherein the microprocessor control system provides analysis of the material response to determine or approximate the tissue material properties.

25. A bioreactor as in claim 1, wherein the sensors include mechanical and nutrient transducers and wherein the microprocessor control system is adapted to provide analysis of the mechanical and nutrient conditioning system transducer signals to determine the tissue growth status.

26. A bioreactor as in claim 1, wherein the microprocessor control uses sensed material properties and/or nutrient conditioning system transducers and a process to alter the mechanical conditioning method and/or nutrient conditioning system conditions to promote optimal tissue growth.

27. A bioreactor as in claim 1, wherein the microprocessor control uses the tissue growth status and a process to alter the mechanical conditioning method and/or nutrient conditioning system conditions to promote optimal tissue growth.

28. A bioreactor for conditioning tissue engineered constructs, comprising:
(a) a bioreactor chamber, the bioreactor chamber including at least one device for holding tissue;
(b) an actuation system including at least one primary mover for applying a mechanical conditioning to the tissue;
(c) a control system for altering biochemistry parameters within the bioreactor chamber and nutrient fluid;
(d) a plurality of sensors including at least one sensor for measuring applied mechanical conditioning and at least one sensor for measuring a tissue response to applied mechanical conditioning;
(e) at least one biochemical condition sensor including at least one sensor for measuring the biochemical parameters within the bioreactor;
(f) microprocessor control system in communication with the actuation system and plurality of sensors for controlling the applied mechanical conditioning and for monitoring response of the tissue;
(g) wherein the microprocessor control system provides real time monitoring and control of conditioning for the tissue within the bioreactor chamber; and
(h) wherein the microprocessor control system is able to programmably adjust or alter conditions for the tissue within the bioreactor chamber in real time based on variations of the mechanical response of the tissue and sensed biochemical conditions using a programmed process, wherein the programmed process incorporates data concerning the tissue within the bioreactor chamber.

29. A bioreactor as in claim 28 wherein the biochemical conditions sensors are selected from the group consisting of sensors for relative humidity, pH, $O_2$, $CO_2$, $N_2$, pressure, temperature and nutrient fluid flow.

30. A bioreactor as in claim 29 wherein at least one of said sensors includes an associated control.

31. A bioreactor as in claim 29 said at least one sensor for measuring applied mechanical conditioning is selected from the group consisting of tissue stress and strain monitors and tissue displacement monitors.

32. A bioreactor as in claim 28 wherein the microprocessor control uses the material properties and/or biochemical condition measurements and a process to alter the conditioning method on a real time basis to promote optimal tissue growth.

* * * * *